(12) United States Patent
Frigg et al.

(10) Patent No.: US 6,821,278 B2
(45) Date of Patent: Nov. 23, 2004

(54) BONE PLATE

(75) Inventors: Robert Frigg, Bettlach (CH); Robert Ferus, Biezwil (CH)

(73) Assignees: Synthes AG CHUR, Chur (CH); Synthes, Paoli, PA (US)

( * ) Notice: Subject to any disclaimer, the term of this patent is extended or adjusted under 35 U.S.C. 154(b) by 80 days.

(21) Appl. No.: 09/994,049

(22) Filed: Nov. 27, 2001

(65) Prior Publication Data
US 2002/0058940 A1 May 16, 2002

Related U.S. Application Data

(63) Continuation of application No. PCT/CH00/00346, filed on Jun. 26, 2000.

(51) Int. Cl.⁷ .................................... A61B 17/58
(52) U.S. Cl. ............................................... 606/69
(58) Field of Search ............................ 606/61, 69, 70, 606/71

(56) References Cited

U.S. PATENT DOCUMENTS

| | | |
|---|---|---|
| 3,552,389 A | 1/1971 | Allgower et al. |
| 3,668,972 A | 6/1972 | Allgower et al. |
| 3,716,050 A | 2/1973 | Johnston |
| 3,779,240 A | 12/1973 | Kondo |
| RE28,841 E | 6/1976 | Allgower et al. |
| 4,219,015 A | 8/1980 | Steinemann |
| 4,408,601 A | 10/1983 | Wenk |
| RE31,628 E | 7/1984 | Allgower et al. |
| 4,493,317 A | 1/1985 | Klaue |
| 4,513,744 A | 4/1985 | Klaue |
| 4,927,421 A | 5/1990 | Goble et al. |
| 5,002,544 A | 3/1991 | Klaue et al. |
| 5,006,120 A | 4/1991 | Carter |
| 5,304,180 A | 4/1994 | Slocum |
| 5,474,553 A | * 12/1995 | Baumgart ............... 606/71 |
| 5,487,743 A | * 1/1996 | Laurain et al. ............ 606/61 |
| 5,601,553 A | 2/1997 | Trebing et al. |
| 5,702,399 A | 12/1997 | Kilpela et al. |
| 5,709,686 A | 1/1998 | Talos et al. |
| 5,741,258 A | * 4/1998 | Klaue et al. ............. 606/70 |
| 5,776,196 A | * 7/1998 | Matsuzaki et al. ....... 623/17.16 |
| 5,810,823 A | 9/1998 | Klaue et al. |
| 5,925,047 A | * 7/1999 | Errico et al. ............. 606/65 |
| 5,938,664 A | 8/1999 | Winquist et al. |
| 5,968,046 A | * 10/1999 | Castleman ............... 606/73 |
| 6,183,475 B1 | 2/2001 | Lester et al. |
| 6,206,881 B1 | * 3/2001 | Frigg et al. ............. 606/69 |
| 6,228,085 B1 | * 5/2001 | Theken et al. ............ 606/61 |

FOREIGN PATENT DOCUMENTS

| | | |
|---|---|---|
| CH | 611147 | 5/1979 |
| DE | 43 41 980 A | 6/1995 |
| DE | 43 43 117 A | 6/1995 |
| DE | 4438264 A1 | 3/1996 |
| EP | 0 207 884 A2 | 1/1987 |
| WO | WO 97/09000 | 3/1997 |

* cited by examiner

Primary Examiner—Eduardo C. Robert
(74) Attorney, Agent, or Firm—Jones Day

(57) ABSTRACT

A bone plate includes an upper surface, a bone-contacting surface, and a plurality of holes extending through the upper and bone-contacting surfaces for receiving bone screws. At least one of the holes includes a protrusion disposed on the bone-contacting surface and at least partially surrounding the hole. The bone plate may define a nominal plate thickness in regions between holes, and the protrusion may define an increased plate thickness that is greater than the nominal plate thickness. A bone plate system including a plurality of bone screws is also disclosed.

25 Claims, 1 Drawing Sheet

BONE PLATE

CROSS-REFERENCE TO RELATED APPLICATIONS

The present application is a continuation of the U.S. National Stage designation of co-pending International Patent Application PCT/CH00/00346, filed Jun. 26, 2000, the entire content of which is expressly incorporated herein by reference thereto.

FIELD OF THE INVENTION

The present invention relates generally to devices for fixation of parts of a to fractured bone and, more specifically, to bone plates and systems for fixation of parts of a fractured bone.

BACKGROUND OF THE INVENTION

Bone plates are commonly used for treatment of a fractured bone. For instance, bone plates may be used in conjunction with bone screws to stabilize parts of a fractured bone. The bone plate may have threaded holes for engaging a threaded screw-head to provide an angularly and axially stable connection between the plate and bone. In this configuration, a certain minimum thickness of the plate is needed in order to provide a secure connection between the bone plate and the screw bead. Otherwise, the connection may lack axial and angular stability. Traditionally, a thick plate has been required to achieve the desired stability of the screw-plate interface. However, it is often not practical for bone plates to be of the required thickness because they may not provide desirable properties, such as flexibility or adaptability. Thus, a need exists for bone plates that are relatively thin, but have holes that provide a stable connection between the plate and screw.

SUMMARY OF THE INVENTION

The present invention is directed to a bone plate having a plurality of holes for receiving bone screws. The bone plate may have an increased thickness in a region surrounding at least one of the holes. This combination of thicknesses is made possible by providing a protrusion formed on one side of the plate that at least partially surrounds the hole. The hole may be provided with a thread or other structure configured and dimensioned to engage a screw-head.

According to one embodiment of the invention, the plate may be thickened by adding a tapered flange protruding from the bone contacting surface of the plate. A corresponding tapered indentation may be provided on the upper surface of the plate, opposite the flange. The flange and/or recess may be formed on the plate, for example, by drawing the plate in the area around the hole.

The protrusion may define an increased plate thickness of the bone plate in the region immediately surrounding the hole, and the bone plate may define a nominal plate thickness is regions spaced from the hole. The increased thickness may be about 1.1 to about 4 times the nominal thickness. Preferably, the increased thickness is about 1.5 to about 2 times the nominal thickness. The protrusion may protrude from the bone contacting surface by about 0.1 to about 3 mm, and preferably by about 0.5 to about 1 mm. The nominal plate thickness may be about 0.5 to about 2 mm, and preferably about 0.8 to about 1.2 mm. In the case where the protrusion is a conical flange, the flange may define an outer conical angle of between about 5° and about 120°, and preferably of between about 40° and about 100°.

As mentioned above, the hole may be provided with at least one internal thread for engaging a portion of a bone screw. The thread may be "straight" provided on the inner surface of a substantially cylindrical hole) or "tapered" (provided on the inner surface of a hole that is tapered or angled with respect to its central axis). One of ordinary skill in the art will know and appreciate, however, that the thread may alternatively be provided in a hole having an inner surface profile that is arcuate, free-form or otherwise shaped and dimensioned. In the case of a tapered thread, the thread preferably tapers radially inward toward the bone-contacting surface. Tapered threads may have a taper angle (indicated as number 13 in FIG. 1) of about 5° to about 50°, and preferably of about 10° to about 30°. According to the exemplary embodiment shown in FIG. 1, taper angle 13 is about 20°. One of ordinary skill in the art will know and appreciate that taper angle 13 may vary along the axis of the hole.

The threads, if provided, may be either single threads or double threads. Single threads may have a pitch of about 0.4 mm to about 1.5 mm, and preferably of about 0.60 mm to about 1.25 mm. Double threads may have a pitch of about 0.2 mm to about 1.5 mm, and preferably of about 0.3 mm to about 0.8 mm. One of ordinary skill in the art will know and appreciate, however, that different pitches may be appropriate for different applications of the bone plate.

According to one embodiment, the axis of the holes may be oriented perpendicular or substantially perpendicular to the upper surface of the plate. In the case where multiple holes are provided, the axes of the holes may be substantially parallel to one another. It should be noted however, that the axes of the holes may alternatively be angled with respect to the plate, and/or to each other.

The present invention is also directed to a bone plate system including at least one bone screw. The bone screw preferably has a thread disposed on its screw-head. In the case where the bone plate is provided with one or more holes having tapered threads, the bone screws to be inserted in those holes are preferably provided with screw-heads having tapered threads as well (i.e., the threads are provided on a tapered screw-head), in which case, the taper angle of the screw-head preferably matches the taper angle of the screw hole. This configuration provides an enlarged engagement surface between the screw-head and the hole, thus allowing more threads to be formed on the hole; ultimately providing improved anchoring of the screw to the bone plate, while maintaining a relatively thin bone plate. This provides advantages such as increased strength of the plate-screw interface, while maintaining the desired mechanical properties of the bone plate, such as flexibility and adaptability to the bone. Thus, the bone plate of the present invention may be advantageously used in applications where a thin bone plate is desirable, such as, for example, with the spinal column, pelvis, or with tubular bones.

BRIEF DESCRIPTION OF THE DRAWINGS

To facilitate an understanding of the characteristics, structure and operation of the invention, preferred features of the invention are described in the accompanying discussion, wherein similar reference characters denote similar elements throughout the several views or embodiments, and wherein.

DETAILED DESCRIPTION OF THE PREFERRED EMBODIMENTS

Figure 1:
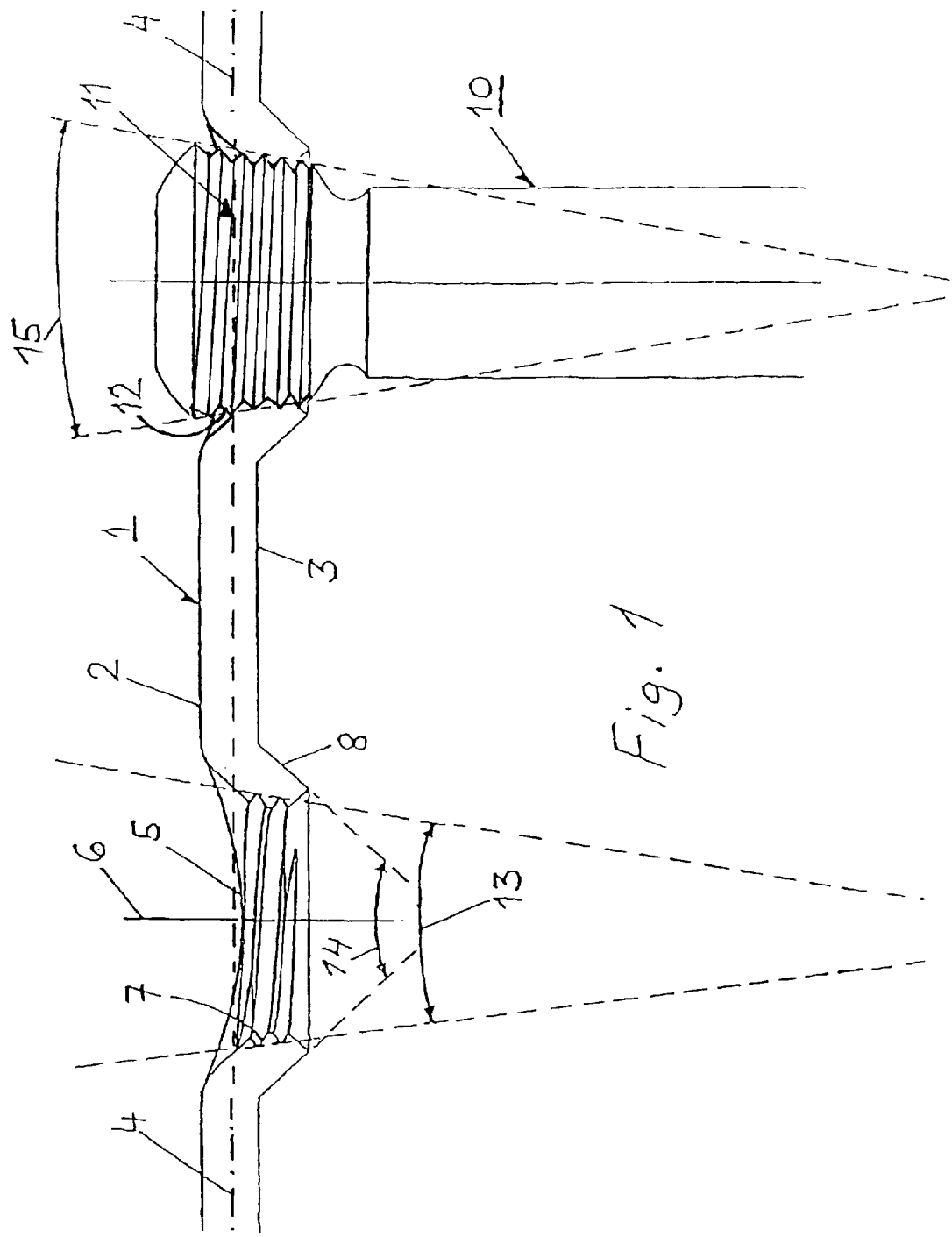
FIG. 1 is a longitudinal cross-section of an illustrative embodiment of a bone plate according to the present invention, shown with a bone screw received in a screw hole.

One embodiment of a bone plate according to the present invention is shown in FIG. 1. Bone plate 1 includes an upper surface 2, a bone-contacting surface 3, and defines a longitudinal axis 4. Bone plate 1 may be formed as a single piece or multiple pieces joined together. A plurality of holes may extend through the upper and bone-contacting surfaces 2, 3. The holes may be spaced apart along longitudinal axis 4, and extend substantially therethrough. While two holes are shown, any number of holes may be provided in bone plate 1, depending on the length of the plate and/or the intended application of the plate.

At least one of the holes, shown as hole 5 in FIG. 1, may be at least partially surrounded by a protrusion 8 that may be formed on one side of plate 1. For example, 30 protrusion 8 may be an annular or partially annular protrusion that at least partially surrounds hole 5. In addition to providing other advantages, discussed herein, protrusion 8 may result in reduced contact area between bone plate 1 and the bone, resulting in improved healing of the bone.

Protrusion 8 is preferably formed on the bone-contacting surface 3. According 35 to one embodiment, protrusion 8 may be a tapered flange, in which case flange 8 may define a taper angle 14 that is preferably about 90°. A corresponding indentation may be provided in the upper surface 2 substantially opposite the flange 8. Preferably, flange 8 and/or the indentation are substantially concentric with respect to central axis 6 of hole 5.

According to one aspect of the invention, plate 1 may define a nominal plate thickness (in the areas between holes) and protrusion 8 may define an increased plate thickness (immediately surrounding hole 5) that is greater than the nominal plate thickness. More specifically, the increased plate thickness may be substantially equal to the nominal plate thickness plus the thickness of the protrusion 8. According to one embodiment, the increased plate thickness may be about 1.1 to about 4 times the nominal thickness, and preferably about 1.5 to about 2 times the nominal thickness. Additionally or alternatively, the nominal plate thickness may be about 0.5 mm to about 2 mm, and preferably about 0.8 mm to about 1.2 mm; and the protrusion may extend from bone-contacting surface (in a direction substantially parallel to central axis 6) by about 0.1 mm to about 3 mm, and preferably by about 0.5 to about 1 mm. According to one preferred embodiment, the nominal thickness is about 1 mm and the protrusion 8 extends from bone-contacting surface 3 by about 0.8 mm, thus providing an increased plate thickness of about 1.8 mm. One of ordinary skill in the art will know and appreciate, however, that protrusion 8 may extend from bone-contacting surface 3 by any amount determined to be suitable for a particular application of plate 1. One of ordinary skill in the art will further know and appreciate that plate 1 may have any nominal thickness determined to be suitable for a particular application of the plate.

Central axis 6 of hole 5 may be oriented substantially perpendicular to the upper and/or bone-contacting surfaces 2, 3. In the case where multiple holes 5 are provided, each hole 5 may define a central axis 6 that is substantially parallel to the axes 6 of adjacent holes 5, although the invention is not limited to this configuration.

Hole 5 may be provided with a plurality of internal threads 7. Threads 7 may taper with respect to central axis 6 (e.g., conical threads) or, alternatively, may be oriented substantially parallel to central axis 6 (e.g., cylindrical threads). In the case where threads 7 taper with respect to central axis 6, threads 7 preferably taper radially inward in a direction toward bone contacting surface 3. According to one embodiment, the taper angle 13 of threads 7 maybe about 5° to about 120°, and preferably about 40° to about 100°. According to one preferred embodiment, taper angle 13 is about 20°, however other values are possible.

Threads 7 may be single threads or double threads, or any other type of thread known to one of ordinary skill in the art. For a single thread, threads 7 may have a pitch of about 0.4 mm to 1.5 mm and, and preferably of about 0.6 mm to about 1.25 mm. For a double thread, threads 7 may have a pitch of about 0.2 mm to about 1.5 mm, and preferably of about 0.3 mm to about 0.8 mm. One of ordinary skill in the art will know and appreciate, however, that threads 7 may have any pitch suitable for a particular application of bone plate 1.

Referring to the right side of FIG. 1, a bone screw 10 is shown inserted in a second hole 5. Screw 10 may have a screw-head 11 with a plurality of external threads 12 disposed thereon. External threads 12 may optionally be tapered threads, and may have a taper angle 15 of between about 5° and about 50°, and preferably between about 10° and about 30°, although other angles are possible. In the case where hole 5 has tapered internal threads 7, taper angle 15 of external threads 12 preferably corresponds to taper angle 13 of internal threads 7. For example, taper angle 15 and taper angle 13 may both be about 20°.

While preferred embodiments and features of the present invention have been disclosed herein, it will be appreciated that numerous modifications and embodiments may be devised by those skilled in the art. It is intended that the appended claims cover all such modifications and embodiments as fall within the true spirit and scope of such claims and that the claims not be limited to or by such preferred embodiments or features.

What is claimed:

1. A bone plate comprising:
    an upper surface;
    a lower surface; and
    a plurality of holes extending through the upper surface and the lower surfaces, the upper surface of the bone plate including a first upper portion and at least one second tapered portion, the at least one second tapered portion located at at least one of the holes and sloping in a direction toward the lower surface such that a gap is formed between the first upper portion of the upper surface of the bone plate and an upper portion of a bone screw securable in the at least one of the holes;
    wherein said at least one of the holes includes a protrusion disposed on the lower surface and at least partially surrounding the hole, and internal threads tapering radially inward in a direction from the upper surface to the lower surface, said sloping direction of said at least one second tapered portion intersects at a non-zero angle with said direction of the tapering internal threads, and the bone plate defines a nominal plate thickness in regions between the holes, and the protrusion defines an increased plate thickness that is about 1.5 to 2 times greater than the nominal plate thickness.

2. The bone plate of claim 1, wherein the nominal plate thickness is about 1 mm and the protrusion extends from the lower surface by about 0.8 mm.

3. The bone plate of claim 1, wherein the protrusion is substantially annular.

4. The bone plate of claim 1, wherein the protrusion minimizes contact between the lower surface and a bone.

5. The bone plate of claim 1, wherein said at least one of the holes defines a central axis, and the protrusion tapers radially inward with respect to the central axis in a direction from the upper surface toward the lower surface.

6. The bone plate of claim 5, wherein the protrusion tapers radially inward, and defines a taper angle of about 40° to about 100°.

7. The bone plate of claim 1, wherein the internal thread is adapted for engaging a threaded screw-head.

8. The bone plate of claim 1, wherein said at least one of the holes defines a central axis, and the internal thread tapers radially inward with respect to the central axis in a direction from the upper surface toward the lower surface.

9. The bone plate of claim 8, wherein the internal thread defines a taper angle of about 10° to about 30°.

10. The bone plate of claim 8, further composing a bone screw having a screw-head with an external thread disposed on the screw-head, wherein said at least one of the holes defines an internal thread taper angle, and the screw-head defines an external thread taper angle that is substantially equal to the internal thread taper angle.

11. The bone plate of claim 10, wherein the internal thread taper angle and the external thread taper angle are about 20°.

12. The bone plate of claim 1, wherein the bone plate defines a longitudinal axis, and the plurality of holes are spaced apart substantially along the longitudinal axis.

13. A bone plate comprising:
an upper surface having a first upper portion;
a lower surface; and
a plurality of threaded holes extending through the upper and lower surfaces, the threaded holes having threads tapering radially inward in a direction from the upper surface to the lower surface for engaging threaded screw-heads; and
a tapered flange formed on the lower surface and at least partially around one of the holes, the tapered flange defining a corresponding tapered portion in the upper surface of the bone plate, the tapered portion sloping in a direction toward the lower surface, such that a gap is formed between the first upper portion of the upper surface of the bone plate and an upper portion of a bone screw secured in the hole said sloping direction intersects at a non-zero angle with said direction of the tapering threads of said one of the holes;
wherein the bone plate defines a nominal plate thickness in regions between the holes, and the tapered flange defines an increased plate thickness that is about 1.5 to 2 times greater than the nominal plate thickness.

14. The bone plate of claim 13, wherein:
said one of the holes defines a central axis;
the tapered flange tapers radially inward with respect to the central axis in a direction from the upper surface toward the lower surface; and
the tapered flange defines a flange taper angle of about 40° to about 100°.

15. The bone plate of claim 14 wherein said one of the holes tapers radially inward with respect to the central axis in a direction from the upper surface toward the lower surface, and the threaded hole defines a threaded hole taper angle of about 10° to about 30°.

16. The bone plate of claim 15, wherein the tapered flange is substantially annular.

17. A bone plate system comprising:
a bone plate including:
an upper surface;
a lower surface;
a plurality of tapered holes tapering radially inward in a direction from the upper and lower surfaces, the holes having an internal thread disposed thereon, and the upper surface of the bone plate including a first upper portion and at least one second tapered portion, the at least one second tapered portion located at at least one of the holes and sloping in a direction toward the lower surface such that a gap is formed between the first upper portion of the upper surface of the bone plate and an upper portion of a bone screw securable in the at least one of the holes, said sloping direction of said at least one second tapered portion intersects at a non-zero angle with said direction of said at least one of the holes; and
an annular protrusion formed at least partially around at least one of the holes and extending from the lower surface, the protrusion being substantially concentric with the hole;
wherein the bone plate defines a nominal plate thickness in regions between the holes, and the protrusion defines an increased plate thickness that is about 1.5 to 2 times greater than the nominal plate thickness; and
a bone screw having a tapered screw-head with an external thread disposed thereon for engaging the internal thread;
wherein the internal thread defines an internal thread taper angle, and the external thread defines an external thread taper angle that is substantially equal to the internal thread taper angle.

18. The bone plate system of claim 17, wherein the annular protrusion tapers radially inward in a direction from the upper surface toward the lower surface.

19. A bone plate comprising:
an upper surface;
a lower surface with a protrusion formed on the lower surface and a threaded hole tapering radially inward through the protrusion in a direction from the upper surface to the lower surface;
wherein the upper surface of the bone plate includes a first upper portion and at least one second tapered portion, located at the threaded hole, sloping in a direction toward the lower surface, such that a gap is formed between the first upper portion of the upper surface of the bone plate and an upper portion of a bone screw secured in the hole said sloping direction of said at least one second tapered portion intersects at a non-zero angle with said direction of said tapering threaded hole; and
wherein the bone plate defines a nominal plate thickness in regions distal to the threaded hole, and the protrusion defines an increased plate thickness that is about 1.5 to 2 times greater than the nominal plate thickness.

20. The bone plate of claim 19, wherein the protrusion is substantially annular, and the threaded hole is coaxial with the protrusion.

21. A bone plate comprising:
an upper surface having a first upper portion and at least one second tapered portion;
a lower surface having a protrusion formed thereon;
a tapered hole tapering radially inward through the protrusion in a direction from the upper surface to the lower surface, the tapered hole having internal threads for engaging a head of a bone screw;
wherein the at least one second tapered portion, located at the tapered hole, slopes in a direction toward the lower surface, such that a gap is formed between the first upper portion of the upper surface of the bone plate and an upper portion of a bone screw secured in the hole, said sloping direction of said at least one second tapered portion intersects at a non-zero angle with said direction of said tapering threaded hole; and wherein the bone plate defines a nominal plate thickness in regions distal to the tapered hole, and the protrusion defines an increased plate thickness that is about 1.5 to 2 times greater than the nominal plate thickness.

22. The bone plate of claim 21, wherein the protrusion is substantially annular.

23. The bone plate of claim 22, wherein the tapered hole is substantially coaxial with the protrusion.

24. The bone plate of claim 21, wherein the tapered hole defines a central axis, and the tapered hole tapers radially inward with respect to the central axis in a direction from the upper surface toward the lower surface.

25. The bone plate of claim 21, wherein the protrusion minimizes contact between the lower surface and a bone.

* * * * *